United States Patent [19]

Nosco

[11] Patent Number: 5,037,631
[45] Date of Patent: Aug. 6, 1991

[54] TECHNETIUM-99M COMPLEX FOR EXAMINATING THE RENAL FUNCTION

[75] Inventor: Dennis L. Nosco, Florissant, Mo.

[73] Assignee: Mallinckrodt Medical, Inc., St. Louis, Mo.

[21] Appl. No.: 605,640

[22] Filed: Oct. 29, 1990

[51] Int. Cl.$^5$ .................. A61K 49/02; C07F 13/00
[52] U.S. Cl. ........................................ 424/1.1; 534/14
[58] Field of Search ...................... 534/147; 424/1.1

[56] References Cited

U.S. PATENT DOCUMENTS 4,849,511  7/1989  Verbruggen ...................... 534/14
4,925,650  5/1990  Nosco et al. ...................... 424/1.1

FOREIGN PATENT DOCUMENTS 173424  3/1986  European Pat. Off. .

Primary Examiner—John S. Maples
Attorney, Agent, or Firm—Daivd A. Key

[57] ABSTRACT

The present invention relates to novel technetium-99m complexes and to methods of preparaing the complexes. The present invention further relates to radiopharmaceutical compositions comprising the complexes, to the use of the compositions for examining the renal function, and to a kit for preparing such compositions.

9 Claims, No Drawings

TECHNETIUM-99M COMPLEX FOR EXAMINATING THE RENAL FUNCTION

The present invention relates to a technetium-99m complex and to a method of preparing the complex. The present invention further relates to a radiopharmaceutical composition comprising the complex, to the use of the composition for examining the renal function, and to a kit for preparing such a composition.

Radioactive labelled compounds are used for the examination of patients, for example, into deviations in shape and function of internal organs and into the presence and location of pathological processes in the body. For this purpose, a composition in which the radioactive compound is present is administered to the patient, for example, in the form of an injectable liquid. By means of suitable detection apparatus, e.g. a gamma camera, images can be obtained of, for example, the organic or the pathological process in which the radioactive compound has been incorporated, by recording the emitted radiation. Compounds which are generally used for examining the renal function are radioactive Tc-99m $MAG_3$, iodo-Hippuran ® and Tc99m-diethylene triamine pentaacetic acid (DTPA), which will be discussed hereinafter.

In addition to the passive glomerular filtration, an active tubular secretion also takes place in the kidneys. The functioning of the kidneys is determined to a considerable extent by this active filtration. In an adult person approximately 125 ml of blood plasma per minute is purified by glomerular filtration. This means that the clearance is 125 ml per minute. The total clearance which can be effected by the kidneys is 600 to 700 ml of plasma per minute. It appears that the above-mentioned chelate of DTPA clears from the kidneys at a rate of 100 ml of blood plasma per minute, and therefore the chelate is eliminated entirely or substantially entirely by glomerular filtration and hence is not very suitable for examining the renal function.

There exists a great need for a suitable composition for examining the renal function which is permanently available, in particular for kidney transplantation patients, accident victims and patients after large vascular operations.

An example of a radioactive iodo-Hippuran ® compound generally used for examining the renal function is iodo-131-Hippuran ®, which is secreted actively tubularly and hence is very suitable for examining the renal function as regards organ specificity. Further, iodo-131-Hippuran ® is excellently suitable for the above applications, because of its ready availability. However, like all iodo-131 compounds, iodo-131-Hippuran ® constitutes a serious radiation burden for the patient. Therefore, iodo-131 compounds can be administered to the patient only in restricted doses, as a result of which the resulting information is insufficient to obtain statistically reliable images of the renal function by means of a gamma camera.

Another radioactive iodo-Hippuran ® compound frequently used for examining the renal function is iodo-123-Hippuran ® which is excellently suitable as regards organ specificity and restricted radiation burden. Iodo-123-containing compositions, however, have only a restricted availability due to the short half-life, i.e. 13.3 hours, and because the production of iodo-123 must necessarily be carried out in a cyclotron.

Technetium-99m complexes which show a tubular secretion which is comparable to that of iodo-Hippuran ® are known from European Patent Application 173424. This application discloses the preparation of Tc-99m-mercaptoaoetyltriglycine (Tc99m-$MAG_3$), which complex is secreted by the kidneys selectively and approximately equally rapidly to iodo-Hippuran ®. However, the organ specificity of said complexes still leaves something to be desired. This is a disadvantage, especially when these compounds are used for function examination. Chemically related compounds having an improved organ specificity are the subject of the recently published European patent application 250013.

In connection with the comparatively short half-life of radionuclides it is often nearly impossible to deliver the ready-to-use labelled product to the user. In such cases it is desirable to place the various reaction components at the user's disposal in a so-called kit. By means of this kit, the user himself can carry out the labelling reaction with the radionuclide in the clinical hospital or laboratory at any desired moment. This is favorable in particular for preparing technetium-99m-labelled products, because most modern clinical hospitals or laboratories have at their disposal a molybdenum-technetium generator, from which the desired quantity of technetium-99m can very easily be obtained in the form of a pertechnetate solution. The process of preparing the technetium-99m-labelled product from the supplied kit must be able to be carried out by the user with a few simple manipulations, without laborious operations, and by using the facilities which are at his disposition in the clinic. Furthermore, the stability of the labelled product is of great importance. In fact, if the stability is not satisfactory, there is insufficient opportunity to be able to prepare and perform the renal function examination in patients carefully. Moreover, there is a constant risk that if the shelf life is exceeded, a contaminated composition may be administered to the patient and the results of the examination will no longer be reliable.

It has now been found that the shelf life of technetium-99m complexes described in the European patent applications mentioned hereinbefore is at most a few hours, depending on the complex-forming ligands and the labelling method used. In practice this is often insufficient because it is desired to have a suitable composition available immediately at any instant of the day. Moreover, it is advantageous that a radioactive composition need be prepared only once daily. Furthermore the reaction conditions in which the user has to prepare the labelled product from the kit are not very favorable. In fact, in order to prepare the technetium-99m complexes described in the European patent applications, the kit constituents must be heated for at least 5 minutes with the eluate from a molybdenum-technetium generator on a boiling water bath to produce the desired reaction resulting in the formation of the technetium-99m complex. In carrying out this operation, the possibility of accidents in which radioactive material is released are very possible.

Technetium-99m complexes for examining the renal function have been previously described in U.S. Pat. No. 4,925,650, which is hereby incorporated by reference. This patent describes technetium-99m complexes having the general formula:

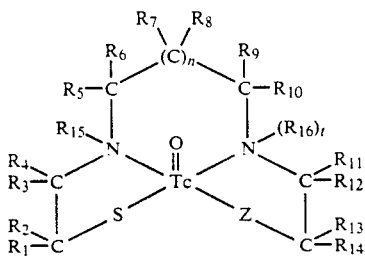

wherein
  Z is a sulphur atom or an amino group of the general formula $R_{17}\text{-N-}(R_{18})_k$, in which k is 0 or 1 and $R_{17}$ and $R_{18}$ have the same meanings as the symbols $R_1$-$R_{16}$;
  each of the symbols $R_1$-$R_{16}$ is individually selected from the group consisting of hydrogen, straight or branched, unsubstituted or substituted alkyl having 1-4 carbon atoms, and ACOOH, wherein A is a straight or branched, unsubstituted or substituted alkyl group having 0-4 carbon atoms;
  and $R_5$ together with $R_6$ or $R_9$ together with $R_{10}$ additionally may form an oxygen atom;
  Tc represents technetium-99m;
  t is 0 or 1; and
  n is 0 or 1;
with the provisos that
  (a) if $R_{15}$, $R_{16}$, $R_{17}$ and/or $R_{18}$ are/is ACOOH, A is a straight or branched, unsubstituted or substituted alkyl group having 1-4 carbon atoms;
  (b) at least one of the symbols $R_1$-$R_{18}$ is ACOOH; and
  (c) if t is 1, at least two of the symbols $R_1$-$R_{18}$ is ACOOH; or a pharmaceutically acceptable salt of this compound.

It is one object of the present invention to provide a technetium-99m complex, suitable for examining the renal function, having a high organ specificity and an improved stability, and which is suitable for preparation from a kit.

The objects of the present invention can be achieved, according to one embodiment of the present invention, by providing a technetium-99m complex which is similar to complexes defined by the general formula (A) above, but wherein certain substitutions have been made.

In particular, the present invention relates to technetiumm-99m complexes which satisfy the general formula:

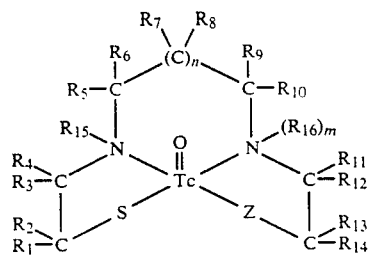

wherein
  each of the symbols $R_1$-$R_{16}$ is individually selected from the group consisting of hydrogen, straight or branched, unsubstituted or substituted alkyl having 1-4 carbon atoms, ACOOH, $ASO_3H$, and $APO_3H$, wherein A is a straight or branched, unsubstituted or substituted alkyl group having 0-4 carbon atoms and wherein H may be replaced with suitable, pharmaceutically acceptable, positively charged ions such as $Na^+$, $K^+$, $Li^+$, $Ca^{2+}$, or $Sr^{2+}$;
  Z is a sulphur atom or an amino group of the general formula $R_{17}\text{-N-}(R_{18})_k$, in which k is 0 or 1 and $R_{17}$ and $R_{18}$ have the same meanings as the symbols $R_1$-$R_{16}$; $R_3$ together with $R_4$, $R_5$ together with $R_6$, $R_9$ together with $R_{10}$, or $R_{11}$ together with $R_{12}$, additionally may form an oxygen atom;
  Tc represents technetium-99m:
  n is 0 or 1; and
  m is 0 or 1;
with the provisos that
  (a) if any of the symbols $R_{15}$-$R_{18}$ is ACOOH, $ASO_3H$, or $APO_3H_2$, then A is a straight or branched, unsubstituted or substituted alkyl group having 1-4 carbon atoms;
  (b) at least one of the symbols $R_1$-$R_{18}$ is ACOOH; and
  (c) at least one of the symbols $R_1$-$R_{18}$ is $ASO_3H$, or $APO_3H_2$.

When the above symbol k is 1, there is a coordinative bond between the amino-N and Tc. The coordinative bonds in the above formula (I) also occur when Z is a sulphur atom.

If the above symbols represent or include substituted alkyl groups, such substituents are preferably selected from hydroxy groups and acid groups or their salts; wherein examples of suitable acid groups are carboxy groups.

Pharmaceutically acceptable salts may be salts with ions of alkali metals, alkaline earths or suitable transition metals.

The new technetium-99m complexes will usually occur in stereoisomeric configurations which may differ in the biological properties. By starting from the stereochemically most suitable complex-forming ligands, stereoisomeric technetium complexes can be prepared having properties which are most favorable for the intended purpose.

While the technetium-99m complexes according to the present invention are similar to those previously described in the U.S. Pat. No. 4,925,650, it has now been discovered that certain substitutions may be made to those complexes which were not previously disclosed. In particular, the complexes according to the present invention include sulfonate or phosphonate groups at the $R_1$ to $R_{16}$ sites.

A preferred technetium-99m complex according to the present invention, satisfies the general formula:

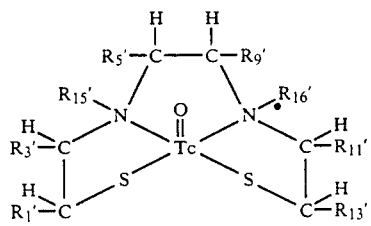

wherein
  each of the symbols $R'_1$, $R'_3$, $R'_5$, $R'_9$, $R'_{11}$, $R'_{13}$, $R'_{15}$, and $R'_{16}$ is individually selected from the group consisting of hydrogen, methyl, $(CH_2)_q COOH$, $(CH_2)_q SO_3H$, and $(CH_2)_q PO_3H_2$, wherein q is 0 or 1; and Tc represents technetium-99m; with the provisos that (a) if either of the symbols R'$_{15}$, or R'$_{16}$ is (CH$_2$)$_q$COOH, (CH$_2$)$_q$SO$_3$H, or (CH$_2$)$_q$PO$_3$H$_2$, then q is 1;

(b) at least one of the symbols R'$_1$, R'$_3$, R'$_5$, R'$_9$, R'$_{11}$', R'$_{13}$, R'$_{15}$, or R'$_{16}$ is (CH$_2$)$_q$COOH;

(c) at least one of the symbols R'$_1$, R'$_3$, R'$_5$, R'$_9$, R'$_{11}$', R'$_{13}$, R$_{15}$' or R$_{16}$' is (CH$_2$)$_q$SO$_3$H, or (CH)$_2$)$_q$PO$_3$H$_2$; and (d) at most four of the symbols R'$_1$, R'$_3$, R'$_5$, R'$_9$, R'$_{11}$', R'$_{13}$, R$_{15}$' or R$_{16}$' are (CH$_2$)$_q$COOH, (CH$_2$)$_q$SO$_3$H, or (CH$_2$)$_q$PO$_3$H$_2$.

A technetiumm-99m complex according to the invention is generally used in the form of a composition which is suitable for examining the renal function. In addition to the radioactive complex, such a radiopharmaceutical composition will usually comprise a liquid, pharmaceutically acceptable carrier material, preferably a physiological saline solution. A radiodiagnostic examination can be performed with such a composition by administering the composition to a patient, in a quantity of 0.1 to 30 mCi, preferably of a 0.5 to 10 mCi, per 70 kg of body weight, and by then recording the radioactive radiation emitted by the living being by means of, for example, a gamma camera.

The invention further relates to a method of preparing a technetium-99m complex according to the invention by reacting technetium-99m in the form of a pertechnetate in the presence of a reducing agent and optionally a suitable chelator with a ligand of the general formula

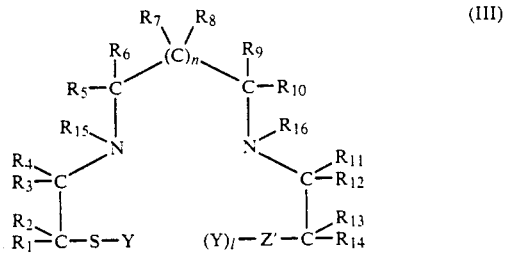

(III)

wherein the symbols n and R$_1$-R$_{16}$ have the same meanings given above in Formula (I);

Z' is a sulphur atom or an amino group of the general formula R$_{17}$-N-R$_{18}$, wherein R$_{17}$ and R$_{18}$ have the same meanings given above in Formula (I);

Y is a hydrogen atom or a suitable protecting group; and l is 0 or 1;

with the provisos that, (a) if Z' is a sulphur atom, then l=1; and (b) if Z' is a amino group, then l=0.

Examples of suitable protective groups Y for the mercapto group are: acetyl, trifluoroacetyl, hydroxyacetyl, carboxyacetyl, acetamidomethyl, benzoyl, benzyl, benzoylaminomethyl and the like.

The reducing agent serves to reduce the Tc-99m pertechnetate which in a physiological saline solution is eluted from a molybdenum-technetium generator. Suitable reducing agents are, for example, dithionite, formamidine sulphinic acid, diaminoethane disulphinate or suitable metallic reducing agents such as Sn(II), Fe(II), Cu(I), Ti(111) or Sb(111); wherein Sn(11) has proved to be particularly suitable.

For the above-mentioned complex-forming reaction, technetium-99m is presented to the above-mentioned ligand as a salt or in the form of a chelate bound to comparatively weak chelators; in the latter case the desired technetium-99m complex is formed by ligand exchange. Examples of suitable chelators for the radionuclide are dicarboxylic acids, polycarboxylic acids or hydroxy carboxylic acids, such as oxalic acid, malonic acid, succinic acid, maleic acid, orthophthalic acid, malic acid, lactic acid, tartaric acid, citric acid, ascorbic acid, salicylic acid or derivatives of these acids; phosphorus compounds such as pyrophosphates; or enolates. Citric acid, tartaric acid, ascorbic acid, glucoheptonic acid or a derivative thereof are particularly suitable chelators for this purpose, because it appears that a chelate of technetium-99m with of one these chelators particularly easily undergoes the desired ligand exchange.

It has been found that the above-mentioned complex-forming reaction occurs quantitatively at room temperature i.e. with a radiochemical yield exceeding 98%. So heating of the reaction mixture is not necessary to reach a full conversion to the desired technetium-99m complex.

Since the radiopharmaceutical composition according to the invention can be prepared so easily and simply, the preparation can be carried out particularly readily by the user himself. The invention therefore also relates to a so-called kit, comprising (1) in an optionally dry condition a ligand of the above general formula III, wherein the symbols have the meanings given hereinbefore and to which optionally an inert, pharmaceutically acceptable carrier and/or auxiliary substances have/has been added, (2) a reducing agent and optionally a chelator, ingredients (1) and (2) being optionally combined, and (3) if desired, instructions for use with a prescription for carrying out the above-described method by reacting ingredients (1) and (2) with technetium-99m in the form of a pertechnetate solution.

Examples of suitable reducing agents and chelators for the above kit have been given hereinbefore. The pertechnetate solution can simply be obtained by the user himself from a molybdenum-technetium generator which is available to him. The above-mentioned ingredients (1) and (2) may be combined, provided they are compatible. Such a monocomponent kit, in which the combined ingredients are preferably lyophilized, is excellently suitable to be reacted by the user with the pertechnetate solution in a simple manner.

The constituent (1) of the above kits may be delivered as a solution, for example, in the form of a physiological saline solution, or in some buffer solution, but is preferably present in a dry condition, for example in a lyophilized condition. When used as a component for an injection liquid, it should be sterile, for example, if the constituent is present in a dry condition, the user should use a sterile physiological saline solution as a solvent. If desired, the above-mentioned constituent may be stabilized in a usual manner with suitable stabilizers such as ascorbic acid, gentisic acid or salts of these acids, or it may be provided with other auxiliary means such as fillers, e.g. glucose, lactose, mannitol, inositol, and the like.

The kit according to the invention preferably comprises a ligand of the general formula

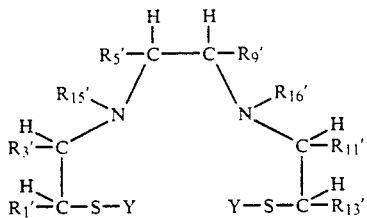

(IV)

wherein
the symbols $R'_1$, $R'_3$, $R'_5$, $R'_9$, $R'_{11}$, $R'_{13}$, $R'_{15}$, and $R'_{16}$ have the same meanings given above in Formula (II); and
Y is a hydrogen atom or a suitable protecting group. These complex-forming ligands can very easily be converted into the desired technetium-99m complexes.

The stereochemical configuration of the technetium-99m complex is determined by the configuration of the starting ligand of the above general formula III or IV. Different stereoisomers of these ligands can be separated from each other by using techniques known for this purpose such as recrystallization and/or chromatographic methods. If desired, for the separation the stereoisomer mixture may be converted with a stereochemically pure D- or L-isomer of a suitable amine, carboxylic acid, and the like, after which the isomer separation is carried out, succeeded by eliminating the used amine, carboxylic acid, etc. An alternative, also particularly suitable method of preparing stereochemically pure ligands, consists in using for the synthesis a starting material which is already stereochemically pure and which is easily available or obtainable as a stereoisomer, and in ensuring that during the synthesis of the intended ligand that the stereochemical purity is not lost, i.e. that no racmization occurs.

The foregoing has been a description of certain preferred embodiments of the present invention, but is not intended to limit the invention in any way. Rather, many modifications, variations and changes in details may be made within the scope of the present invention.

What is claimed is:

1. A technetium-99m radiopharmaceutical complex for examining the renal function, said complex having the formula:

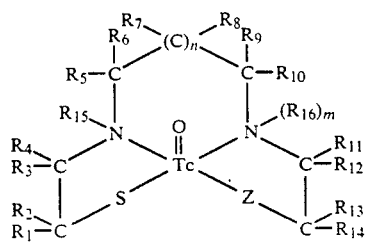

wherein
each of the symbols $R_1$–$R_{16}$ is individually selected from the group consisting of hydrogen, straight or branched, unsubstituted or substituted alkyl having 1–4 carbon atoms, $ACOOH$, $ASO_3H$, and $APO_3H_2$, wherein A is a straight or branched, unsubstituted or substituted alkyl group having 0–4 carbon atoms and wherein H may be replaced with suitable, pharmaceutically acceptable, positively charged ions such as $Na^+$, $K^+$, $Li^+$, $Ca^{2+}$, or $Sr^{2+}$;

Z is a sulphur atom or an amino group of the general formula $R_{17}$-N-$(R_{18})_k$, wherein k is 0 or 1 and $R_{17}$ and $R_{18}$ have the same meanings as the symbols $R_1$–$R_{16}$;

$R_3$ together with $R_4$, $R_5$ together with $R_6$, $R_9$ together with $R_{10}$, or $R_{11}$ together with $R_{12}$, additionally may form an oxygen atom;

Tc represents technetium-99m;

n is 0 or 1; and m is 0 or 1;

with the provisos that
if any of the symbols $R_{15}$–$R_{18}$ is $ACOOH$, $ASO_3H$, or $APO_3H_2$, then A is a straight or branched, unsubstituted or substituted alkyl group having 1–4 carbon atoms;

at least one of the symbols $R_1$–$R_{18}$ is $ACOOH$; and at least one of the symbols $R_1$–$R_{18}$ is $ASO_3H$, or $APO_3H_2$.

2. A complex according to claim 1, wherein said substituted alkyl group is selected from the group consisting of hydroxy groups and acid groups, or their salts.

3. A complex according to claim 2, wherein said acid group is carboxy group.

4. A complex according to claim 2, wherein said salts may be pharmaceutically acceptable salts with ions of alkali metals, alkaline earths, or suitable transition metals.

5. A complex according to claim 1, having the formula:

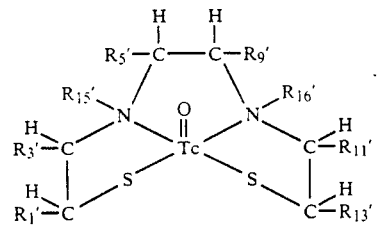

wherein
each of the symbols $R'_1$, $R'_3$, $R'_5$, $R'_9$, $R'_{11}$, $R'_{13}$, $R'_{15}$, and $R'_{16}$ individually separated from the group consisting of hydrogen, methyl, $(CH_2)_qCOOH$, $(CH_2)_qSO_3H$, and $(CH_2)_qPO_3H_2$, wherein q is 0 or 1; and Tc represents technetium-99m; with the provisos that
if either of the symbols $R'_{15}$, or $R'_{16}$ is $(CH_2)_qCOOH$, $(CH_2)_qSO_3H$, or $(CH_2)_qPO_3H_2$, then q is 1;

at least one of the symbols $R'_1$, $R'_3$, $R'_5$, $R'_9$, $R'_{11}$, $R'_{13}$, $R'_{15}$ or $R'_{16}$ is $(CH_2)_qCOOH$, at least one of the symbols $R'_1$, $R'_3$, $R'_5$, $R'_9$, $R'_{11}$, $R'_{13}$, $R_{15}'$ or $R_{16}'$ is $(CH_2)_qSO_3H$, cc $(CH_2)_qPO_3H_2$; and at most four of the symbols $R'_1$, $R'_3$, $R'_5$, $R'_9$, $R'_{11}$, $R'_{13}$, $R_{15}$ or $R_{16}'$ are $(CH_2)_qCOOH$, $(CH_2)_qSO_3H$, or $(CH_2)_qPO_3H_2$.

6. A method of examining the renal function using a radiopharmaceutical complex comprising:
providing a radiopharmaceutical complex having the formula:

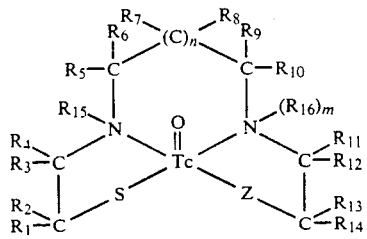

wherein
each of the symbols $R_1$–$R_{16}$ is individually selected from the group consisting of hydrogen, straight or branched, unsubstituted or substituted alkyl having 1–4 carbon atoms, ACOOH, $ASO_3H$, and $APO_3H_2$, wherein A is a straight or branched, unsubstituted or substituted alkyl group having 0–4 carbon atoms and wherein H may be replaced with suitable, pharmaceutically acceptable, positively charged ions such as $Na^+$, $K_+$, $Li^+$, $Ca^{2+}$, or $Sr^{2+}$;

Z is a sulphur atom or an amino group of the general formula $R_{17}$-N-$(R_{18})_k$, wherein k is 0 or 1 and $R_{17}$ and $R_{18}$ have the same meanings as the symbols $R_1$–$R_{16}$;

$R_5$ together with $R_6$ or $R_9$ together with $R_{10}$ additionally may form an oxygen atom;

To represents technetiumm-99m;

n is 0 or 1; and m is 0 or 1;

with the provisos that
if any of the symbols $R_{15}$–$R_{18}$ is ACOOH, $ASO_3H$, or $APO_3H_2$, then A is a straight or branched, unsubstituted or substituted alkyl group having 1–4 carbon atoms;

at least one of the symbols $R_1$–$R_{18}$ is ACOOH; and at least one of the symbols $R_1$–$R_{18}$ is $ASO_3H$, or $APO_3H_2$;

administering an effective amount of said radiopharmaceutical complex to a living being; and scanning said living being with detection means to detect said administered radiopharmaceutical complex.

7. A method according to claim 6, wherein said complex has the formula:

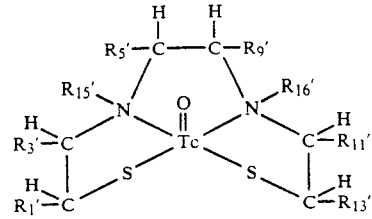

wherein
each of the symbols $R'_1$, $R'_3$, $R'_5$, $R'_9$, $R'_{11}$, $R'_{13}$, $R'_{15}$, and $R'_{16}$ is individually selected from the group consisting of hydrogen, methyl, $(CH_2)_q COOH$, $(CH_2)_q SO_3H$, and $(CH_2)_q PO_3H_2$, wherein q is 0 or 1; and Tc represents technetium-99m; with the provisos that
if either of the symbols $R'_{15}$, or $R'_{16}$ is $(CH_2)_q COOH$, $(CH_2)_q SO_3H$, or $(CH_2)_q PO_3H_2$, then q is 1;

at least one of the symbols $R'_1$, $R'_3$, $R'_5$, $R'_9$, $R'_{11}$, $R'_{13}$, $R'_{15}$, or $R'_{16}$ is $(CH_2)_q COOH$;

at least one of the symbols $R'_1$, $R'_3$, $R'_5$, $R'_9$, $R'_{11}$, $R'_{13}$, $R_{15}'$ or $R_{16}'$ is $(CH_2)_q SO_3H$, or $(CH_2)_q PO_3H_2$; and at most four of the symbols $R'_1$, $R'_3$, $R'_5$, $R'_9$, $R'_{11}$, $R'_{13}$, $R_{15}'$ or $R_{16}'$ are $(CH_2)_q COOH$, $(CH_2)_q SO_3H$, or $(CH_2)_q PO_3H_2$.

8. A method according to claim 6, wherein said complex is administered in a quantity of 0.1 to 30 mCi per 70 kg of body weight.

9. A method according to claim 8, wherein said complex is administered in a quantity of 0.5 to 10 mCi per 70 kg of body weight.

* * * * *